US012622957B2

(12) United States Patent
Szczepanek et al.

(10) Patent No.: US 12,622,957 B2
(45) Date of Patent: May 12, 2026

(54) Mycoplasma VACCINE COMPOSITION AND METHODS

(71) Applicant: UNIVERSITY OF CONNECTICUT, Farmington, CT (US)

(72) Inventors: Steven M. Szczepanek, Coventry, CT (US); Steven J. Geary, Mansfield, CT (US); Edan R. Tulman, Mansfield, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 890 days.

(21) Appl. No.: 17/782,447

(22) PCT Filed: Dec. 3, 2020

(86) PCT No.: PCT/US2020/062994
§ 371 (c)(1),
(2) Date: Jun. 3, 2022

(87) PCT Pub. No.: WO2021/113433
PCT Pub. Date: Jun. 10, 2021

(65) Prior Publication Data
US 2023/0029948 A1 Feb. 2, 2023

Related U.S. Application Data

(60) Provisional application No. 62/943,052, filed on Dec. 3, 2019.

(51) Int. Cl.
*A61K 39/02* (2006.01)
*A61P 31/04* (2006.01)

(52) U.S. Cl.
CPC .......... *A61K 39/0241* (2013.01); *A61P 31/04* (2018.01)

(58) Field of Classification Search
None
See application file for complete search history.

(56) References Cited

FOREIGN PATENT DOCUMENTS

EP 1808490 A2 7/2007

OTHER PUBLICATIONS

Smith et al. JAMA vol. 199, No. 6, Feb. 6, 1967 (Year: 1967).*
N view of Mara et al. npj Vaccines 2020 (31) (Year: 2020).*
Bajantri B, Toolsie O, Venkatram S, Diaz-Fuentes G. Mycoplasma Pneumoniae Pneumonia: Walking Pneumonia Can Cripple the Susceptible. J Clin Med Res. Dec. 2018;10(12):891-897. doi: 10.14740/jocmr3592w. Epub Oct. 30, 2018. PMID: 30425761; PMCID: PMC6225856.

Liu X, Jiang Y, Chen X, Li J, Shi D, Xin D. Drug resistance mechanisms of Mycoplasma pneumoniae to macrolide antibiotics. Biomed Res Int. 2014;2014:320801. doi: 10.1155/2014/320801. Epub Jan. 28, 2014. PMID: 24592385; PMCID: PMC3925631.
Niederman M. in the clinic. Community-acquired pneumonia. Ann Intern Med. Oct. 6, 2009;151(7):ITC4-2-ITC4-14; quiz ITC4-16. doi: 10.7326/0003-4819-151-7-200910060-01004. Erratum in: Ann Intern Med. Dec. 1, 2009;151(11):827. PMID: 19805767.
Proft T, Herrmann R. Identification and characterization of hitherto unknown Mycoplasma pneumoniae proteins. Mol Microbiol. Jul. 1994; 13(2):337-48. doi: 10.1111/j.1365-2958.1994.tb00427.x. PMID: 7984111.
Smith CB, Friedewald WT, Chanock RM. Inactivated Mycoplasma pneumoniae vaccine. Evaluation in volunteers. JAMA. Feb. 6, 1967;199(6):353-8. PMID: 5334595.
Waites KB, Xiao L, Liu Y, Balish MF, Atkinson TP. Mycoplasma pneumoniae from the Respiratory Tract and Beyond. Clin Microbiol Rev. Jul. 2017;30(3):747-809. doi: 10.1128/CMR.00114-16. PMID: 28539503; PMCID: PMC5475226.
International Search Report and Written Opinion for PCT/US2020/062994 dated Mar. 16, 2021.
Sakthi, S. et al., Lipoprotein LpqS deficient M. tuberculosis mutant is attenuated for virulence in vivo and shows protective efficacy better than BCG in guinea pigs, Vaccine, Jan. 5, 2016, vol. 34, pp. 735-743 (Abstract Only).
Szczepanek, S. M. et al, Vaccination of BALB/c mice with an avirulent Mycoplasma pneumoniae P30 mutant results in disease exacerbation upon challenge with a virulent strain. Infect Immun. Mar. 2012;80(3):1007-14. doi: 10.1128/IAI.06078-11. Epub Jan. 17, 2012. PMID: 22252865; PMCID: PMC3294651.
Becker, K. et al., 'Mycobacterium tuberculosis lipoproteins in vimlence and immunity-fighting with a double edged sword', FEBS letters, Nov. 2016, vol. 590, pp. 3800-3819.
Leng, C.-H. et al., 'Recombinant bacterial lipoproteins as vaccine candidates', Expert review of vaccines, Sep. 2015, vol. 14,No. 12,pp. 1623-1632 (Abstract Only).
Mara, A. B. et al., Lipid moieties of Mycoplasma pneumoniae lipoproteins are the causative factor of vaccine-enhanced disease, npj Vaccines, 2020 [epub Apr. 8, 2020 , vol. 5, No. 31, pp. 1-5.
Bryson, D. G., et al., "Pathology of Induced Mycoplasma Bovis Calf Pneumonia in Experimentally Vaccinated Animals," Mycoplasmas of ruminants: pathogenicity, diagnostics, epidemiology and molecular genetics. 1999. vol. 3, pp. 128-132.
Mulongo, M., et al., "Vaccination of Cattle with the N Terminus of LppQ of *Mycoplasma mycoides* subsp. *mycoides* Results in Type III Immune Complex Disease upon Experimental Infection," Infection and Immunity, May 2015, vol. 83, No. 5, pp. 1992-2000.
Nicholas, R. A. J., et al., "An inactivated whole cell vaccine and LppQ subunit vaccine appear to exacerbate the effects of CBPP in adult cattle," Report of the 3rd Meeting of the FAO-OIE-AU/IBAR-IAEA Consultative Group on Contagious Bovine Pleuropneumonia (CBPP). 91-97 (2004).

(Continued)

*Primary Examiner* — Jana A Hines
*Assistant Examiner* — Khatol S Shahnan Shah
(74) *Attorney, Agent, or Firm* — CANTOR COLBURN LLP

(57) ABSTRACT
Described are vaccine compositions, methods of manufacture thereof, and methods of treating or preventing certain bacterial infections in humans and other mammals. For example, described are compositions comprising bacterial cell extracts that have undergone pretreatment such that lipid moieties have been cleaved from bacterial lipoproteins, thereby forming a vaccine composition that can stimulate a desired mammalian immune response while avoiding unwanted negative effects.

12 Claims, 13 Drawing Sheets

(56)     References Cited

OTHER PUBLICATIONS

Razin, S., et al., "Molecular Biology and Pathogenicity of Mycoplasmas," Microbiology and Molecular Biology Reviews, Dec. 1998, p. 1094-1156.

Rosenbusch, R., "Test of an Inactivated Vaccine Against Mycoplasma bovis Respiratory Disease by Transthoracic Challenge with an Abscessing Strain," Abstracts of the 12th International Organization of Mycoplasmology Conference, Sydney, Australia, Jul. 22-28, 1998, p. 185.

* cited by examiner

Outside Bacterial Cell

Inside Bacterial Cell

*Mycoplasma* VACCINE COMPOSITION AND METHODS

CROSS-REFERENCE TO RELATED APPLICATIONS

The present application is a National Stage Entry of PCT/US2020/062994, filed 3 Dec. 2020, published as WO 2021/113433 A1, which claims the benefit of and priority to U.S. Provisional Patent Application Ser. No. 62/943,052 filed: 3 Dec. 2019 and titled: Mycoplasma Vaccine Composition and Methods, each of which is incorporated herein by reference in its entirety.

BACKGROUND

1. Field of the Discovery

Described are vaccine compositions, methods of manufacture thereof, and methods of treating or preventing certain bacterial infections in humans and other mammals.

2. Background Information

Respiratory tract infections (RTIs) are the leading infectious-disease cause of death among children and the elderly, and fifth-leading cause of death overall, in the world today. (Niederman M, *Ann. Intern. Med.* 2009; 151(7):ITC4-1).

The mollicute pathogen *Mycoplasma pneumoniae* is a major cause of dangerous RTIs, including pneumonia, and is responsible for over two million infections and 100,000 hospitalizations in the United States every year. (Waites, K. B., Xiao, L., Liu, Y., Balish, M. F., & Atkinson, T. P. (2017). *Clinical Microbiology Revs.,* 30(3), 747-809). Additionally, mortality rates from *M. pneumoniae* pneumonia are very high, especially among children and elderly persons. (Bajantri B, Toolsie O, Venkatram S, Diaz-Fuentes G. *J. Clin. Med. Res.* 2018; 10(12):891-97).

*M. pneumoniae* is highly transmissible through airborne fluid droplets from sneezing, coughing, or speaking, leading to rapidly spreading local epidemics in close-community environments such as schools, households, assisted living facilities, barracks, and dormitories.

Besides infecting a large number of individuals, *M. pneumoniae* infection is very difficult to treat. Mollicute bacteria such as *M. pneumoniae* lack a peptidoglycan cell wall, a common drug target for antibiotic treatment using β-lactam antibiotics. Extant strains of *M. pneumoniae* are also beginning to exhibit resistance to macrolides and other treatment options. (Liu X, Jiang Y, Chen X, Li J, Shi D, Xin D. *Biomed. Res. Int.* 2014; 2014:320801).

The high morbidity rate and numerous infection treatment hurdles suggest that a preventative *M. pneumoniae* vaccine would be very desirable.

Unfortunately, previous attempts to create an *M. pneumoniae* vaccine failed because, for then-unknown reasons, experimental *M. pneumoniae* vaccines frequently exacerbated the disease among vaccinated individuals who later became infected. For example, in a 1967 clinical study a substantial percentage of volunteer patients who received an experimental vaccine suffered worse *M. pneumoniae* disease than patients who did not receive the vaccine. (Smith C B, Friedewald W T, Chanock R M. *J. Am. Med. Ass'n,* 199 (1967), 353-58). Recent studies have recapitulated this vaccine-enhanced disease (VED) phenomenon in mouse model. (Szczepanek S M et al., *Infect Immun.* 2012 March; 80(3): 1007-14).

These serious challenges highlight the grave importance of developing an efficacious, safe vaccine against mollicute bacteria such as *M. pneumoniae*.

SUMMARY

In certain aspects, the description provides a vaccine composition comprising de-lipidated bacteria material, e.g., bacteria, bacterial extract or bacterial lysate. In any of the aspects or embodiments described herein, the bacteria material may comprise live whole-cell bacteria, killed/inactivated whole-cell bacteria, whole-cell extract, fractions of whole-cell extract (e.g., aqueous fraction, nonaqueous fraction, insoluble fraction, etc.), components of fractionated whole-cell extract, admixtures from fractionated whole-cell extract, isolated bacterial proteins (such as, e.g., lipoproteins), fragments of bacterial proteins (such as, e.g., fragments of lipoproteins), lipid-associated membrane proteins (LAMPs), fragments of LAMPs, fractions having had LAMPs removed/extracted, and any combination thereof.

In any of the described aspects or embodiments, the bacteria material may be completely de-lipidated or partially de-lipidated; completely non-lipidated or partially non-lipidated; and any combination thereof.

In any of the described aspects or embodiments, the vaccine composition may further comprise one or more adjuvants. In any of the described aspects or embodiments, the adjuvant may comprise monophosphoryl lipid A (MPLA), aluminum derivatives (aluminum hydroxide, aluminum sulfate, aluminum phosphate, or potassium aluminum sulfate), oil-in-water emulsion composed of squalene (MF59), bacterial/viral Cystine phosphate Guanosine (CpG) derivatives (e.g. CpG 1018), Chilean soapbark tree extract (QS-21) or a combination thereof. Contemplated herein is the use of suitable adjuvants currently known or that become known.

In any of the described aspects or embodiments, the bacteria material comprises material derived from a mollicute bacterium. In any of the described aspects or embodiments, the bacteria material comprises material derived from the genus *Mycoplasma*. In any of the described aspects or embodiments, the bacteria material comprises material derived from at least one of wildtype or synthetic strains of *Mycoplasma pneumoniae, Mycoplasma genitalium, Ureaplasma urealvticum, Mycoplasma hominis Mycoplasma gallisepticum, Mycoplasma pulmonis*, or any combination thereof.

In any of the described aspects or embodiments, the vaccine composition further comprises one or more suitable solvents, for example, sterile water, sterile saline, calcium carbonate, xanthan, succinate buffer, adjuvant solution, other vaccines, etc.

In any of the described aspects or embodiments, the vaccine composition further comprises one or more suitable carriers, such as, for example, viral or bacterial vectors, plasmids, RNA replicons, etc.

In any of the described aspects or embodiments, the vaccine composition further comprises one or more suitable preservatives or excipients, including, by way of example, gelatin, carbohydrates, neomycin, formaldehyde, albumin, cellulose, sodium carbonate, Tween 80, etc.

In any of the described aspects or embodiments, the vaccine composition may be packed into a suitable delivery vehicle such as, e.g., aqueous solution, nonaqueous solution, tincture, pill, tablet, powder, nanoparticle, capsule, gel, cream, implant, or suppository.

In any of the described aspects or embodiments, the vaccine composition may be loaded into a suitable patient-delivery apparatus, such as, e.g., a hypodermic syringe, intravenous drip, nasal syringe, pipette, eye dropper, inhaler, atomizer, or dermal patch.

In additional aspects, the present description further provides a method of manufacturing a vaccine. In any of the aspects or embodiments described herein, the method of manufacture described herein comprises the steps of providing or preparing a bacterial material, e.g., a mollicute bacteria material; and treating the bacteria material to reduce or remove at least a portion or all of the bacterial lipoprotein lipid moieties that are ordinarily bound to mollicute bacterial membrane lipoproteins from the bacterial material (i.e., de-lipidating), treating the bacterial material to reduce or remove at least a portion or all of the membrane-associated lipoproteins or a combination thereof.

The removal may be accomplished either in vitro or in vivo. For example, in any of the described aspects or embodiments, the method of manufacture, removing some or all of lipid moieties from the lipoproteins may be accomplished by any suitable ex vivo/in vitro de-lipidation method such as, e.g., bacterial lipoprotein lipase (LPL) hydrolysis digestion or other suitable method of cleaving or degrading lipid moieties. In any of the described aspects or embodiments, entire lipoproteins including their bound lipid moieties are fractioned, extracted, or removed from the bacteria material.

In any of the described aspects or embodiments, the method of manufacture of a de-lipidated bacteria material, the step of treating the bacteria material to remove some or all of the bacterial lipoprotein lipid moieties from the bacterial material may be accomplished by any suitable in vivo method such as, e.g., genetic/epigenetic modification and/or knockout in the bacteria from which the lipoproteins are derived, RNA silencing, posttranslational modification, or proteolysis.

In any of the described aspects or embodiments, the method of manufacture, bacteria whole-cell extracts are fractionated. In any of the described aspects or embodiments, the fractionation may be accomplished using a solvent including a non-ionic detergent, e.g., Triton™ X-114. In any of the described aspects or embodiments, de-lipidation may be accomplished before fractionation or after fractionation. In any of the described aspects or embodiments, fractionation may be performed using high-performance liquid chromatography (HPLC) or ultra-high-performance liquid chromatography (UHPLC).

In any aspect or embodiment described herein, the de-lipidated bacteria material is combined with one or more adjuvants. In any of the described aspects or embodiments, the adjuvant may comprise MPLA, aluminum derivatives (aluminum hydroxide, aluminum sulfate, aluminum phosphate, or potassium aluminum sulfate), oil-in-water emulsion composed of squalene (MF59), bacterial/viral Cystine phosphate Guanosine (CpG) derivatives (e.g. CpG 1018), Chilean soapbark tree extract (QS-21), or a combination thereof. Contemplated herein is the use of suitable adjuvants currently known or that become known.

In any of the described aspects or embodiments, the bacteria material of the present method comprises material derived from a mollicute. In certain aspects, the bacteria material of the present method comprises material derived from the genus *Mycoplasma*. In certain aspects, the bacteria material of the present method comprises material derived from wildtype or synthetic strains of *Mycoplasma pneumoniae, Mycoplasma gallisepticum, Mycoplasma pulmonis,*

*Mycoplasma genitalium, Ureaplasma urealyticum, Mycoplasma hominis*, or any combination thereof.

In any of the described aspects or embodiments, the method of manufacture further comprises combining the de-lipidated bacteria material with one or more suitable solvents.

In any of the described aspects or embodiments, the method of manufacture further comprises combining the de-lipidated bacteria material with one or more suitable carriers.

In any of the described aspects or embodiments, the method of manufacture further comprises combining the de-lipidated bacteria material with one or more suitable preservatives.

In any of the described aspects or embodiments, the method of manufacture further comprises packing the de-lipidated bacteria material into a suitable delivery means such as, e.g., aqueous solution, nonaqueous solution, tincture, pill, tablet, powder, nanoparticle, capsule, gel, cream, implant, or suppository.

In any of the described aspects or embodiments, the method of manufacture further comprises loading the de-lipidated bacteria material into a suitable patient-delivery apparatus, such as, e.g., a hypodermic syringe, intravenous drip, nasal syringe, pipette, eye dropper, inhaler, atomizer, or dermal patch.

In an additional aspect, the present description provides methods of treating or preventing mollicute infection, e.g., respiratory tract infection (RTI) such as pneumonia, in a subject, e.g., a mammal including a human. In an exemplary embodiment, the method of treatment or prevention comprises administering to a subject a therapeutically effective amount of a vaccine, the vaccine comprising de-lipidated bacteria material with or without non-lipidated bacteria material as described herein, wherein the vaccine is effective for treating or preventing a mollicute infection in the subject.

In any of the aspects or embodiments described herein, the mollicute infection is a respiratory tract infection (RTI), e.g., a *M. pneumoniae* RTI.

In any of the aspects or embodiments described herein, the subject is a mammal, such as a human. In certain embodiments, the subject is an adolescent human. In any of the aspects or embodiments described herein, the subject is in need of treatment or prevention of an RTI.

In an additional exemplary embodiment, the disclosure provides a method of preventing a mollicute RTI comprising administering to a subject in need thereof, a prophylactically effective amount of vaccine, the vaccine comprising de-lipidated bacteria material with or without non-lipidated bacteria material as described herein, wherein the vaccine is effective for preventing a mollicute RTI in the subject. In any of the aspects or embodiments described herein, the subject is a mammal, such as a human (adult or adolescent).

In any aspect or embodiment described herein, the vaccine may be administered parenterally, intravenously, intramuscularly, subcutaneously, nasally, dermally, orally, or rectally.

In any aspect or embodiment described herein, the vaccine may be administered using a hypodermic syringe, intravenous drip, nasal syringe, pipette, eye dropper, inhaler, atomizer, or dermal patch.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the present disclosure may be utilized in numerous combinations, all of which are expressly contemplated by the present description. These additional advantages objects and embodiments are expressly included within the scope of the present disclosure. The publications and other materials used herein to illuminate the background of the present disclosure, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the present disclosure. The drawings are only for the purpose of illustrating an embodiment of the present disclosure and are not to be construed as limiting the present disclosure.

DETAILED DESCRIPTION

Figure 1:
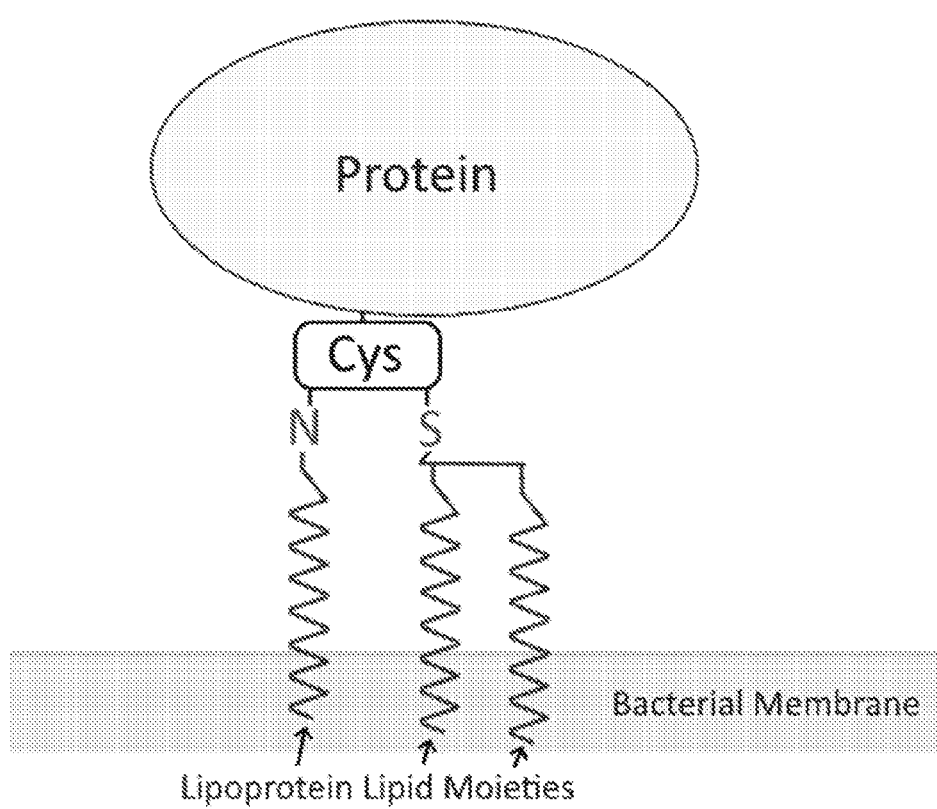
FIG. 1 depicts an illustrative diagram of a bacterial membrane-associated lipoprotein.
Figure 2:
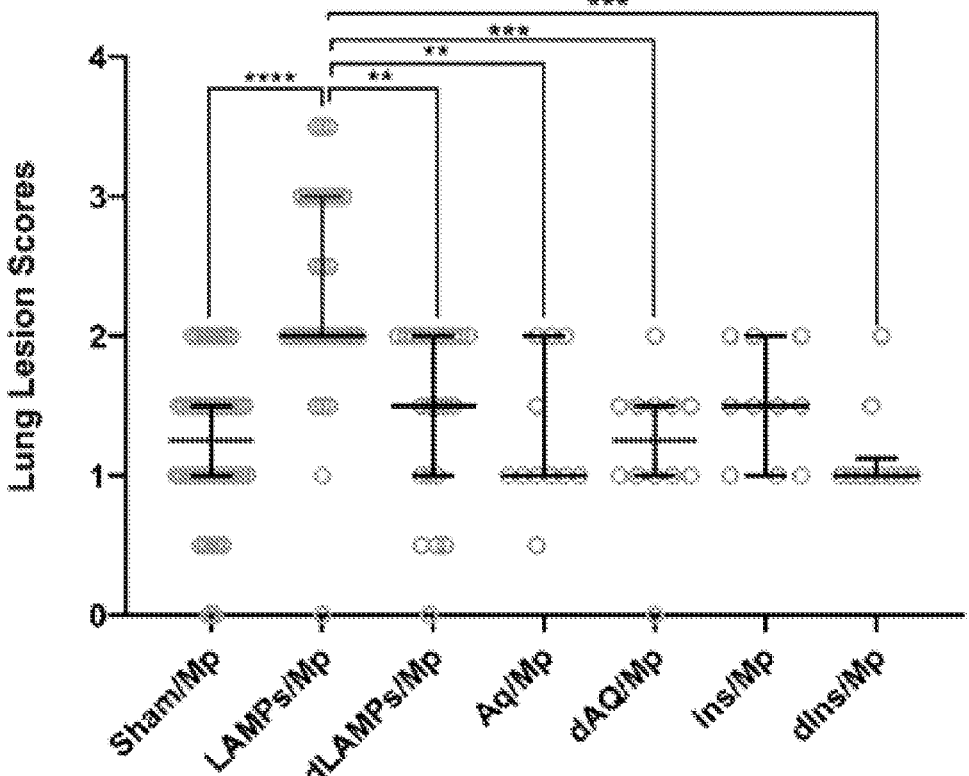
FIG. 2 is a graphical representation of experimental data, indicating relative lung lesion scores of vaccinated and subsequently-challenged mice. Each point represents an individual animal. Error bars indicate median and interquartile ranges (IQR).
Figure 3:
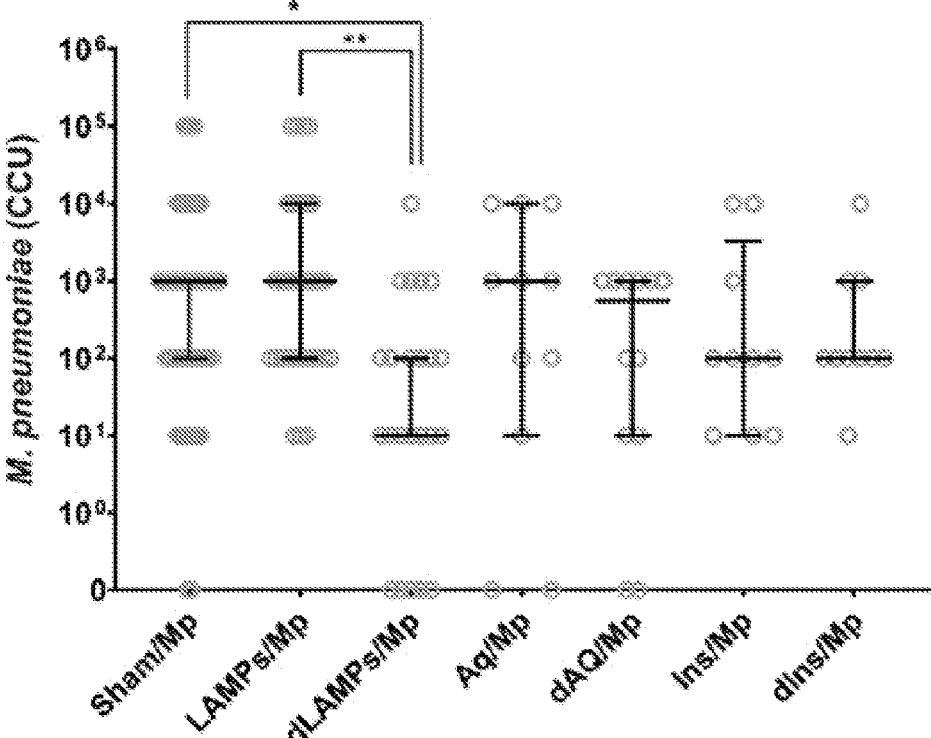
FIG. 3 is a graphical representation of experimental data, indicating relative *M. pneumoniae* loads, measured in color-changing units (CCU). Each point represents an individual animal. Error bars indicate median and IQR.
Figure 4:
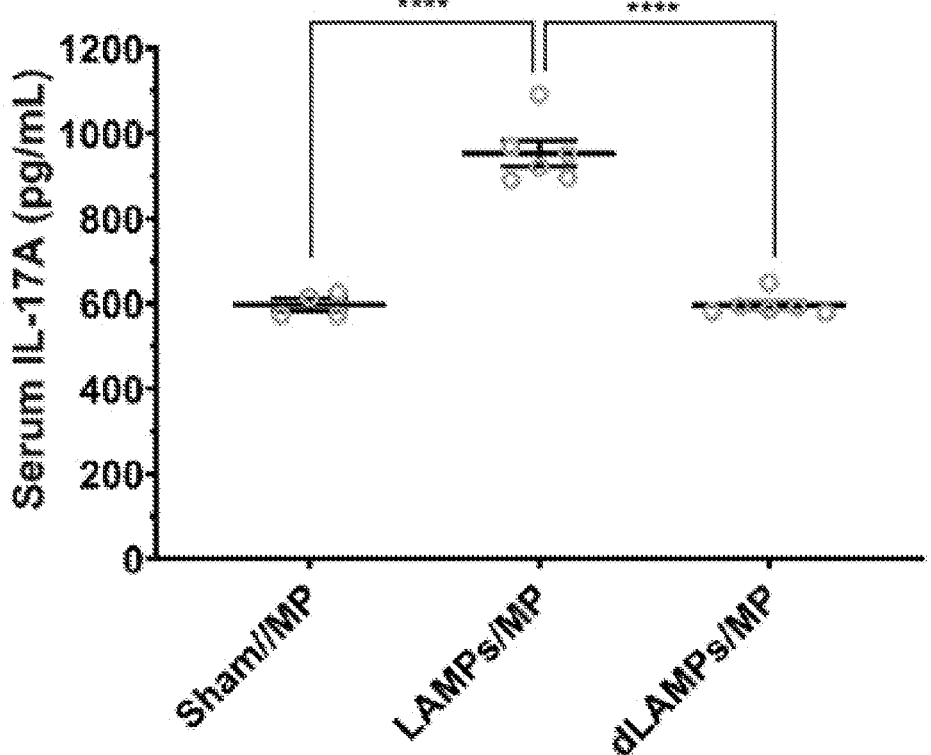
FIG. 4 is a graphical representation of experimental data, indicating relative serum IL-17A levels in *M. pneumoniae* challenged mice that had been vaccinated with negative control, lipid-intact LAMPs, and de-lipidated LAMPs. Error bars indicate mean and standard error of the mean (SEM).
Figure 5:
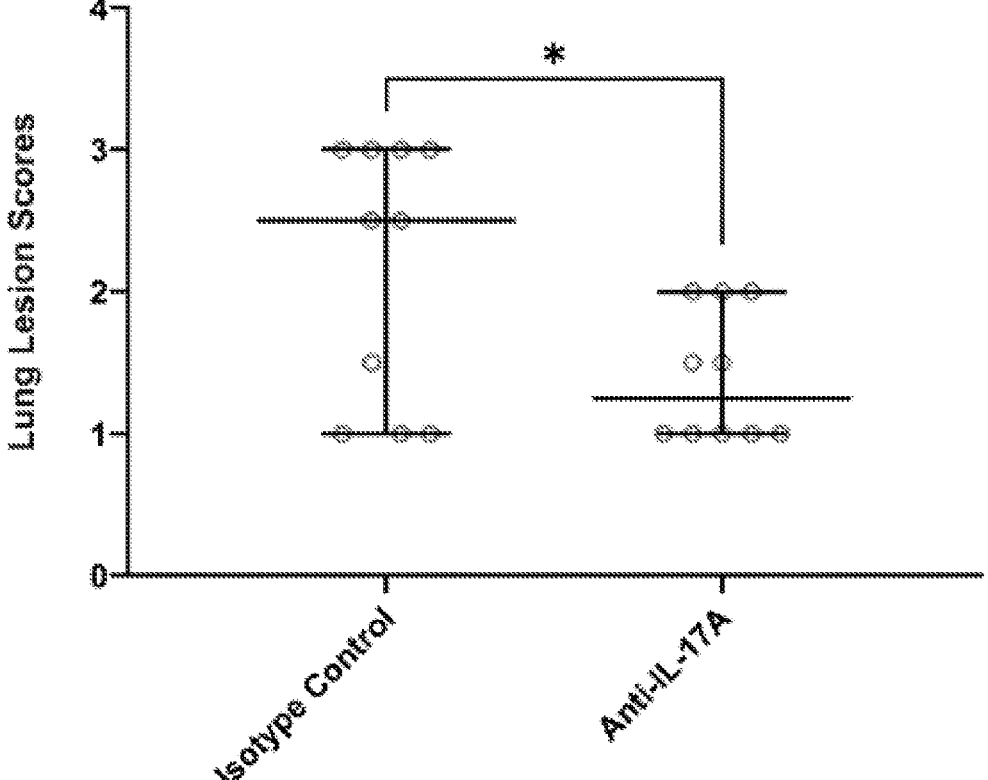
FIG. 5 is a graphical representation of experimental data, indicating relative post-infection lung lesion scores of lipid-intact-LAMP-vaccinated mice that were treated or untreated with anti-IL-17A antibody. Each point represents an individual animal. Error bars indicate median and IQR.
Figure 6:
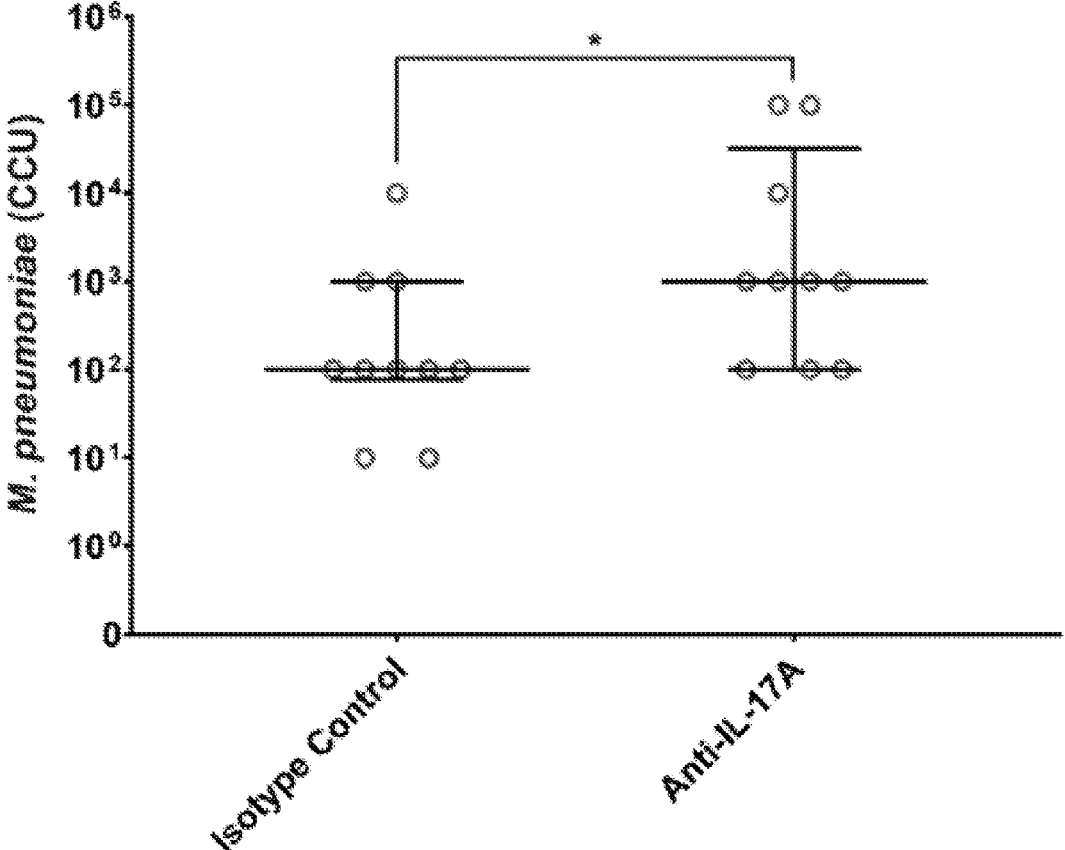
FIG. 6 is a graphical representation of experimental data, indicating relative *M. pneumoniae* loads in lipid-intact-LAMP-vaccinated mice that were treated or untreated with anti-IL-17A antibody. Each point represents an individual animal. Error bars indicate median and IQR.
Figure 7:
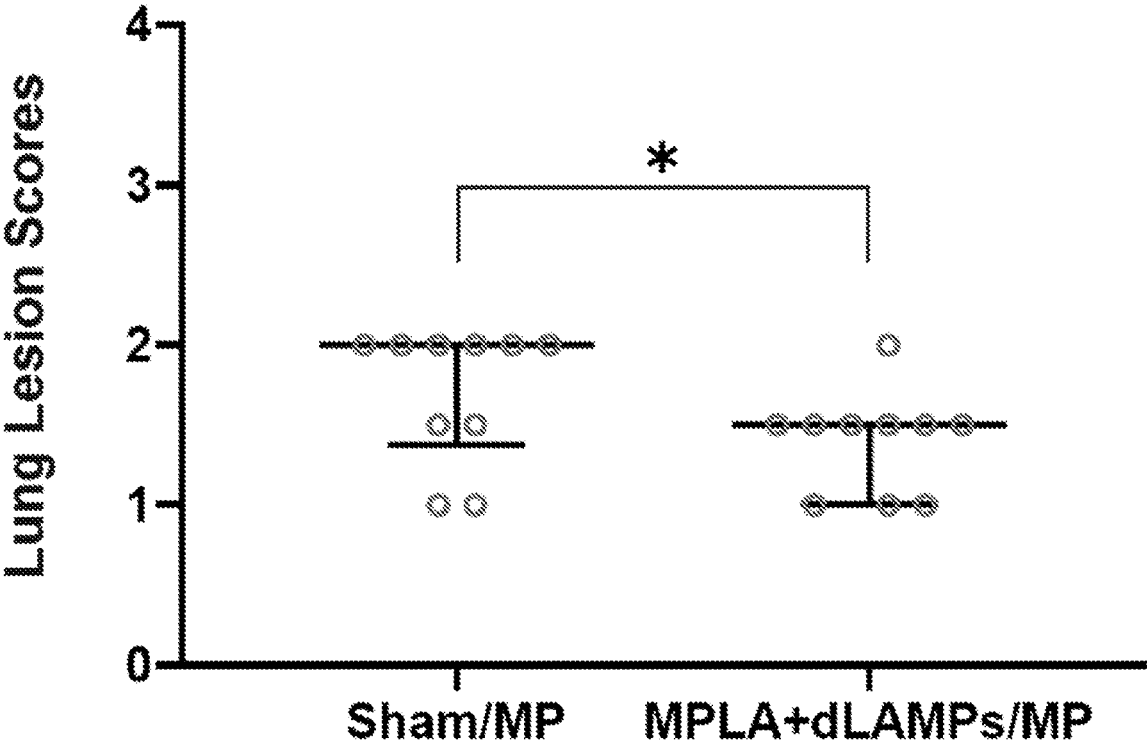
FIG. 7 is a graphical representation of experimental data, indicating relative post-infection lung lesion scores of control mice and mice that had been vaccinated with a dLAMP+MPLA vaccine. Each point represents an individual animal. Error bars indicate median and IQR.
Figure 8:
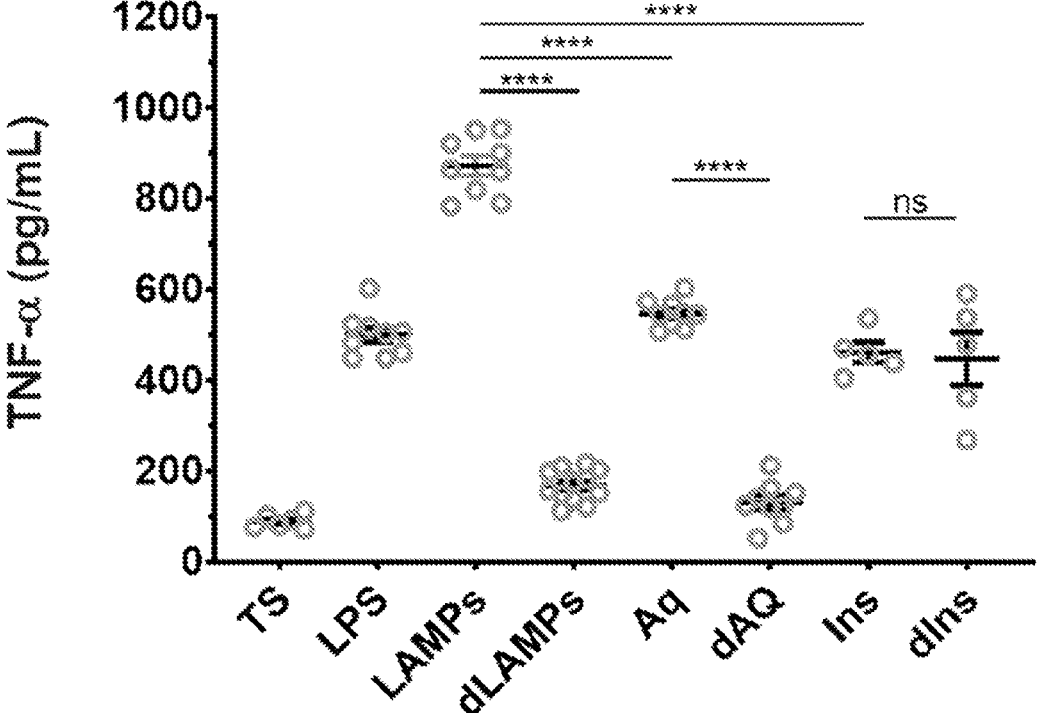
FIG. 8 is a graphical representation of experimental data, indicating supernatant TNF-α levels produced by murine J774A.1 macrophages stimulated by intact or lipase-treated *M. pneumoniae* Triton™ X-114-derived fractions. Error bars indicate mean and SEM.
Figure 9:
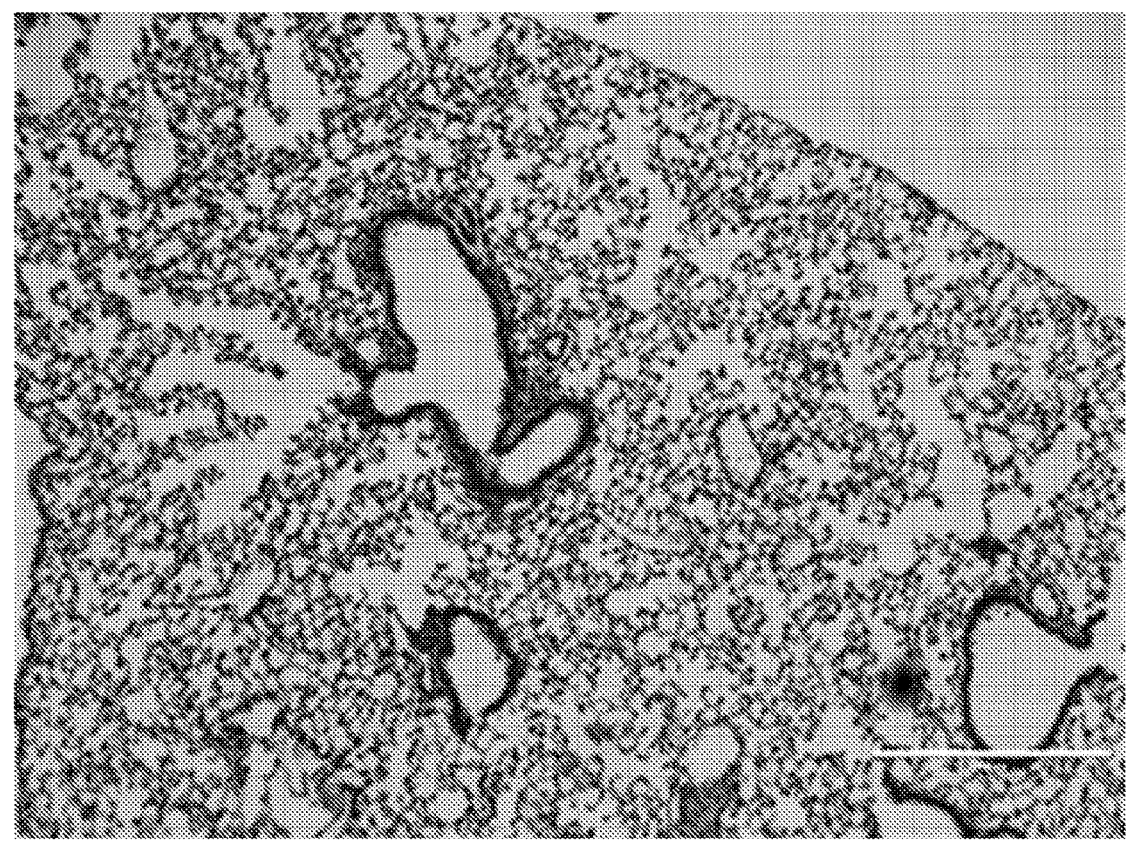
FIG. 9 is an illustrative histological micrograph depicting healthy murine lung tissue.
Figure 10:
FIG. 10 is an illustrative histological micrograph of lipid-intact-LAMP-vaccinated, subsequently-challenged mouse lung, depicting lung tissue having multiple lung lesions.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

Unless otherwise defined, all technical and scientific terms used herein have the same meaning as commonly understood by one of ordinary skill in the art to which this invention belongs. The following references, the entire disclosures of which are incorporated herein by reference, provide one of skill with a general definition of many of the terms (unless defined otherwise herein) used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, the Harper Collins Dictionary of Biology (1991). Generally, the procedures of molecular biology methods described or inherent herein and the like are common methods used in the art. Such standard techniques can be found in reference manuals such as for example Sambrook et al., (2000, Molecular Cloning—A Laboratory Manual, Third Edition, Cold Spring Harbor Laboratories); and Ausubel et al., (1994, Current Protocols in Molecular Biology, John Wiley & Sons, New-York).

The terminology used in the description is for describing particular embodiments only and is not intended to be limiting of the invention. Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The term "about" as it is used herein, in association with numeric values or ranges, reflects the fact that there is a certain level of variation that is recognized and tolerated in the art due to practical and/or theoretical limitations. For example, minor variation is tolerated due to inherent variances in the manner in which certain devices operate and/or measurements are taken. In accordance with the above, the phrase "about" is normally used to encompass values within the standard deviation or standard error.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration", "co-administered" and "co-administering" or "combination therapy" refer to both concurrent administration (administration of two or more agents at the same time) and time varied administration (administration of one or more agents at a time different from that of the administration of an additional agent or agents), so long as the agents are administered to some extent, preferably at effective amounts, at the same time. In certain preferred aspects, one or more of the present agents described herein, are co-administered in combination with at least one additional bioactive agent, especially including an antifungal, antibacterial, antibiotic, antiviral, and/or biocide.

As used herein, the term "bacteria material" refers to any live whole-cell bacteria, killed/inactivated whole-cell bacteria, lysate, whole-cell extract, fractions of whole-cell extract (e.g., aqueous fraction, nonaqueous fraction, insoluble fraction, etc.), components of fractionated whole-cell extract, admixtures from fractionated whole-cell extract, isolated bacterial proteins (such as, e.g., lipoproteins), fragments of bacterial proteins (such as, e.g., fragments of lipoproteins), lipid-associated membrane proteins (LAMPs), fragments of LAMPs, fractions having had LAMPs removed/extracted, and any combination thereof. Bacteria material may be from any synthetic or wildtype strain of bacteria.

The term "vaccine" means any substance that may be used to stimulate an animal's physiological response providing an increase in the animal's immunity or resistance to a disease. A vaccine may prevent initial infection or onset of a disease state in an animal, or may reduce the severity or duration of a disease state in an animal. The conferred immunity or resistance may be temporary, semi-permanent, or permanent.

The term "adjuvant" means an additive or supplement that increases in effectiveness of a medical treatment such as a vaccine inoculation.

The term "respiratory tract infection" (RTI) means any infectious disease of an animal's upper or lower respiratory tract, including, e.g., rhinitis, rhinosinusitis, laryngitis, pharyngitis, tonsillitis, tracheitis, tracheobronchitis, bronchitis, bronchiolitis, and pneumonia.

The term "pneumonia" means an infection of the lungs caused by a virus, bacteria, or other microorganism. The term "community-acquired pneumonia" (CAP) means any form of pneumonia infection that is contracted by a person or other mammal having had little contact with the healthcare system, i.e., in contrast with hospital-acquired pneumonia (HAP).

The term "vaccine-enhanced disease" (VED) refers to the tendency for an infection occurring subsequent to vaccination to exhibit a more severe pathology in some or all vaccinated individuals than in individuals who were not vaccinated. It is possible that a vaccine may confer some immunity (i.e., resistance to acquiring an infection) and cause VED (i.e., among vaccinated individuals who do acquire an infection, the infection tends to be more severe than infections in unvaccinated individuals).

"Mollicute" refers to a class of Gram-stain-negative bacteria distinguished by very small cell size, typically in the range of 200 nm to 300 nm in diameter; small genome size, typically in the range of about 600 to 2,500 kbp; absence of a peptidoglycan cell wall; and, typically, a cell membrane having relatively high sterol content. Mollicute genera include, e.g., *Mycoplasma, Phytoplasma*, and *Ureaplasma*.

A "de-lipidated" bacteria cell, cell extract, mixture, or lipoprotein is one that has been treated or otherwise modified, for example by lipase digestion, such that at least a portion or all of the lipoproteins that are ordinarily bound to lipid moieties are not bound to such moieties, leaving only the peptide portion of the lipoproteins.

The term "non-lipidated," as used herein, refers to a bacteria cell, cell extract, mixture, or lipoprotein that has been modified in vivo, for example by genetic modification, RNA silencing, post-translation modification, or proteolysis, such that lipoproteins are either unexpressed or, if expressed, lack lipid moieties that are found in homologous wildtype bacteria strains.

The term "lipoprotein-associated membrane protein" (LAMP) refers to any hydrophobic membrane-embedded surface lipoprotein, with or without the lipid moieties bound thereto. The term "de-lipidated lipoprotein-associated membrane protein" (dLAMP) refers to LAMPs that have had lipid moieties partially or completely removed, cleaved, or degraded therefrom.

The term "effective amount/dose," "pharmaceutically effective amount/dose," "pharmaceutically effective amount/dose" or "therapeutically effective amount/dose" unless the context indicates otherwise can mean, but is in no way limited to, that amount/dose of the active pharmaceutical ingredient sufficient to prevent, inhibit the occurrence, ameliorate, delay or treat (alleviate a symptom to some extent, preferably all) at least one symptom of a condition, disorder or disease state. As used herein, the term "prophylactically effective amount" can mean that amount/dose of the active pharmaceutical ingredient sufficient to prevent the occurrence, ameliorate or delay at least one symptom of the condition, disorder or disease state or prevent the condition, disorder or disease state.

The effective amount depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 1000 mg/kg body weight/day of active ingredients is administered dependent upon potency of the agent. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosages for use in humans. The dosage of such compounds lies preferably within a range of circulating concentrations that include the ED50 with little or no toxicity. The dosage may vary within this range depending upon the dosage form employed and the route of administration utilized. For any compound used in the method of the present disclosure, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The term "pharmacological composition," "therapeutic composition," "therapeutic formulation" or "pharmaceutically acceptable formulation" can mean, but is in no way limited to, a composition or formulation that allows for the effective distribution of an agent provided by the present disclosure, which is in a form suitable for administration to the physical location most suitable for their desired activity, e.g., systemic administration.

The term "pharmaceutically acceptable" or "pharmacologically acceptable" can mean, but is in no way limited to, entities and compositions that do not produce an adverse, allergic or other untoward reaction when administered to an animal, or a human, as appropriate.

The term "pharmaceutically acceptable carrier" or "pharmacologically acceptable carrier" can mean, but is in no way limited to, any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "systemic administration" refers to a route of administration that is, e.g., enteral or parenteral, and results in the systemic distribution of an agent leading to systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect. Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compounds of the instant disclosure can potentially localize the drug, for example, in certain tissue types, such as the tissues of the reticular endothelial system (RES). A liposome formulation which can facilitate the association of drug with the surface of cells, such as, lymphocytes and macrophages is also useful. The term "local administration" refers to a route of administration in which the agent is delivered to a site that is apposite or proximal, e.g., within about 10 cm, to the site of the lesion or disease.

Reference will now be made in detail to exemplary embodiments of the invention. While the invention will be described in conjunction with the exemplary embodiments, it will be understood that it is not intended to limit the invention to those embodiments. To the contrary, it is intended to cover alternatives, modifications, and equivalents as may be included within the spirit and scope of the invention as defined by the appended claims.

Previous attempts to create a *Mycoplasma pneumoniae* vaccine failed because the vaccine caused VED in a substantial number of trial patients. Recent research has surprisingly and unexpectedly demonstrated that the cause of *Mycoplasma* VED is the lipid moieties bound to membrane-embedded lipoproteins, which may be generally referred to as lipoprotein-associated membrane proteins (LAMPs). More particularly, *Mycoplasma* LAMP lipid moieties induce an over exuberant response of the pro-inflammatory cytokine interleukin-17A (IL-17A), which in turn causes recruitment of immune cells such as monocytes and neutrophils. Recent IL-17A research has demonstrated the IL-17A response is responsible for causing VED. Accordingly, averting the IL-17A response, for example by eliminating the lipid moieties that trigger the response, could beneficially prevent VED.

Following this surprising and unexpected discovery, research indicated that removing or degrading lipid moieties from LAMPs found in whole-cell *Mycoplasma* bacteria, *Mycoplasma* whole-cell extracts, or fractions thereof prevents the IL-17A response and alleviates VED risk. Further, research has shown that de-lipidated *Mycoplasma* material elicits an effective immunogenic response and confers significant *Mycoplasma* immunity. Thus, de-lipidated material derived from mollicute bacteria such *Mycoplasma* is suitable for creating a safe and effective *Mycoplasma* vaccine.

Exemplary compositions and methods of the present invention are described in more detail below.

In certain aspects, the description provides a vaccine composition comprising de-lipidated bacteria material. In any of the aspects or embodiments described herein, the bacteria material may comprise live whole-cell bacteria, killed/inactivated whole-cell bacteria, whole-cell extract, fractions of whole-cell extract (e.g., aqueous fraction, insoluble fraction, etc.), components of fractionated whole-cell extract, admixtures from fractionated whole-cell extract, isolated bacterial proteins (such as, e.g., lipoproteins), fragments of bacterial proteins (such as, e.g., fragments of lipoproteins), lipid-associated membrane proteins (LAMPs), fragments of LAMPs, fractions having had LAMPs removed/extracted, and any combination thereof. Bacteria material may be from any synthetic or wildtype strain of bacteria.

In any of the described aspects or embodiments, the bacteria material may be completely de-lipidated or partially de-lipidated; completely non-lipidated or partially non-lipidated; and any combination thereof.

For example, in any of the described aspects or embodiments, the bacteria material of the vaccine composition may be 100 percent de-lipidated, about 100 percent de-lipidated, about 95 percent de-lipidated, about 90 percent de-lipidated, about 85 percent de-lipidated, about 80 percent de-lipidated, about 75 percent de-lipidated, about 70 percent de-lipidated, about 65 percent de-lipidated, about 60 percent de-lipidated, about 55 percent de-lipidated, about 50 percent de-lipidated, about 45 percent de-lipidated, about 40 percent de-lipidated, about 35 percent de-lipidated, about 30 percent de-lipidated, about 25 percent de-lipidated, about 20 percent de-lipidated, about 15 percent de-lipidated, about 10 percent de-lipidated, about 5 percent de-lipidated, or about 1 percent de-lipidated. A percent of de-lipidation refers to percent of lipid moieties removed from membrane-associated lipoproteins that are present in an initial bacteria material.

In any of the described aspects or embodiments, the bacteria material may be completely non-lipidated or partially non-lipidated. For example, in any of the described aspects or embodiments, the bacteria material of the vaccine composition may be 100 percent non-lipidated, about 100 percent non-lipidated, about 95 percent non-lipidated, about 90 percent non-lipidated, about 85 percent non-lipidated, about 80 percent non-lipidated, about 75 percent non-lipidated, about 70 percent non-lipidated, about 65 percent non-lipidated, about 60 percent non-lipidated, about 55 percent non-lipidated, about 50 percent non-lipidated, about 45 percent non-lipidated, about 40 percent non-lipidated, about 35 percent non-lipidated, about 30 percent non-lipidated, about 25 percent non-lipidated, about 20 percent non-lipidated, about 15 percent non-lipidated, about 10 percent non-lipidated, about 5 percent non-lipidated, or about 1 percent non-lipidated. A percent of non-lipidation refers to a percent reduction in lipid moieties present in a bacteria material relative to wildtype.

Any of the above examples may be combined in any desired combination such that, for example, a composition can be produced including a portion of treated bacteria material having about 60 percent non-lipidated bacteria material may include a portion of treated bacteria material having about 60 percent de-lipidated bacteria material.

In any of the described aspects or embodiments, the vaccine composition may further comprise one or more adjuvants. In any of the described aspects or embodiments, the adjuvant may comprise monophosphoryl lipid A (MPLA), an aluminum salt, or other adjuvant. In any of the described aspects or embodiments, the adjuvant may comprise MPLA, aluminum derivatives (aluminum hydroxide, aluminum sulfate, aluminum phosphate, or potassium aluminum sulfate), oil-in-water emulsion composed of squalene (MF59), bacterial/viral Cysteine phosphate Guanosine (CpG) derivatives (e.g. CpG 1018), Chilean soapbark tree extract (QS-21), or a combination thereof. Contemplated herein is the use of suitable adjuvants currently known or that become known.

In any of the described aspects or embodiments, the bacteria material comprises material derived from a synthetic or wildtype mollicute bacteria. In certain aspects, the bacteria material comprises material derived from synthetic or wildtype bacteria of the genus *Mycoplasma*. In certain aspects, the bacteria material comprises material derived from synthetic or wildtype strains of *Mycoplasma pneumoniae, Mycoplasma gallisepticum, Mycoplasma pulmonis, Mycoplasma genitalium, Ureaplasma urealyticum, Mycoplasma hominis* or any combination thereof. It will be understood to those skilled in the art that microorganisms such as bacteria are likely to vary in genetic sequence and phenotype to a tolerable degree from cell to cell. For instance, all various strains of *Mycoplasma pneumoniae*, while possessing some differences, are all understood to those skilled in the art to fall within the scope of the term "*Mycoplasma pneumoniae.*"

In any of the described aspects or embodiments, the vaccine composition further comprises one or more suitable solvents, for example, sterile water, sterile saline, calcium carbonate, xanthan, succinate buffer, adjuvant solution, other vaccines, etc. or a combination thereof.

In any of the described aspects or embodiments, the vaccine composition further comprises one or more suitable carriers, such as, for example, viral or bacterial vectors, plasmids, RNA replicons, etc. or a combination thereof.

In any of the described aspects or embodiments, the vaccine composition further comprises one or more suitable preservatives (e.g., stabilizer) or excipients, including, by way of example, gelatin, carbohydrates, neomycin, sorbitol, formaldehyde, albumin, cellulose, sodium carbonate, Tween 80, etc. or a combination thereof.

In any of the described aspects or embodiments, the vaccine composition further comprises one or more suitable carriers.

In any of the described aspects or embodiments, the vaccine composition further comprises one or more suitable preservatives, such as, e.g., anti-fungal agents.

In any of the described aspects or embodiments, the vaccine composition may be packed into a suitable delivery vehicle such as, e.g., aqueous solution, nonaqueous solution, tincture, pill, tablet, powder, nanoparticle, capsule, gel, cream, implant, or suppository.

In any of the described aspects or embodiments, the vaccine composition may be loaded into a suitable patient-delivery apparatus, such as, e.g., a hypodermic syringe, intravenous drip, nasal syringe, pipette, eye dropper, inhaler, atomizer, or dermal patch.

In an additional aspect, the present description further provides methods of manufacturing a vaccine. In any of the described aspects or embodiments, the method comprises providing or preparing a bacteria material, e.g., mollicute bacteria material, treating the bacteria material to reduce or remove at least a portion of the lipid moieties that are ordinarily bound to bacteria membrane lipoproteins, treating the bacteria material to reduce or remove at least a portion of the membrane-associated lipoproteins or a combination thereof.

In any of the described aspects or embodiments, wherein the mollicute bacteria is of the genus *Mycoplasma*. In any of the described aspects or embodiments, wherein the mollicute bacteria is of the species *Mycoplasma pneumoniae*.

In any of the aspects or embodiments described herein, the step of treating the bacteria material, e.g., mollicute bacteria material, to reduce or remove at least a portion of the lipid moieties that are ordinarily bound to bacteria membrane lipoproteins includes treating or digesting the bacteria material with a bacterial lipoprotein lipase.

In any of the aspects or embodiments described herein, the step of treating the bacteria material, e.g., mollicute bacteria material, to reduce or remove at least a portion of the membrane-associated lipoproteins includes genetically knocking down or knocking out the bacteria cells' lipoprotein genes.

In any of the aspects or embodiments described herein, the step of treating the bacteria material, e.g., mollicute bacteria material, to reduce or remove at least a portion of the membrane-associated lipoproteins includes performing RNA interference or silencing of the bacteria cells' lipoprotein genes.

In any of the aspects or embodiments described herein, the step of treating the bacteria material, e.g., mollicute bacteria material, to reduce or remove at least a portion of the membrane-associated lipoproteins includes performing transposase mutagenesis.

In any of the aspects or embodiments described herein, the method further comprises a step of combining the treated mollicute bacteria material with one or more solvents.

In any of the aspects or embodiments described herein, the method further comprises a step of combining the treated mollicute bacteria material with one or more buffers.

In any of the aspects or embodiments described herein, the method further comprises a step of combining the treated mollicute bacteria material with one or more stabilizers.

In any of the aspects or embodiments described herein, the method further comprises a step of combining the treated mollicute bacteria material with one or more carriers.

In any of the aspects or embodiments described herein, the method further comprises a step of combining the treated mollicute bacteria material with one or more preservatives.

In any of the aspects or embodiments described herein, the method further comprises a step of packing the treated mollicute bacteria material into a delivery vehicle.

In any of the described aspects or embodiments, the methods may be accomplished in vitro or in vivo. For example, in any of the aspects or embodiments described herein, de-lipidation may be accomplished by any suitable ex vivo/in vitro de-lipidation method such as, e.g., bacterial lipoprotein lipase (LPL) hydrolysis digestion or other suitable method of cleaving or degrading lipid moieties. In an alternative embodiment, entire lipoproteins including their bound lipid moieties are fractioned, extracted, or removed from the bacteria material, leaving behind a bacteria material derivative having no detectible lipoproteins.

In any of the aspects or embodiments described herein, de-lipidation may be accomplished by any suitable in vivo method such as, e.g., genetic/epigenetic modification and/or knockout in the bacteria from which the lipoproteins are derived, RNA silencing, posttranslational modification, or proteolysis. It will be readily understood by those having skill in the art that such genetic/epigenetic modification may be effectuated by any suitable molecular genetics tool and/or vector and/or mutagenesis tool, including, e.g., CRISPR, transcription activator-like effector nuclease (TALEN), zinc finger nuclease (ZNF), meganuclease, transposon, or retrotransposon.

In any of the aspects or embodiments described herein, bacteria whole-cell extracts are fractionated. In certain aspects, the fractionation may be accomplished using a non-ionic detergent solution, e.g., Triton™ X-114. In any of the aspects or embodiments described herein, de-lipidation may be accomplished before fractionation or after fractionation. In any of the aspects or embodiments described herein, fractionation may be performed using high-performance liquid chromatography (HPLC) or ultra-high-performance liquid chromatography (UHPLC).

In any aspect or embodiment, the de-lipidated bacteria material is combined with one or more adjuvants. In any of the described aspects or embodiments, the adjuvant may comprise MPLA or other known adjuvant, e.g., those described herein, or that becomes known.

In a non-limiting exemplary embodiment of the present method of manufacture, whole-cell extract of *M. pneumoniae* is fractionated using a non-ionic detergent solution, e.g., Triton™ X-114 solvent. The fraction containing LAMPs is separated using filter-aided sample preparation (FASP) and treated with bacterial lipoprotein lipase (LPL) to de-lipidate the LAMPs. The de-lipidated LAMPs are added to 0.9% physiological saline solution at a concentration of about 200 µg/mL. MPLA adjuvant is added to the dLAMP+ saline solution at a concentration of about 80 µg/mL. Persons skilled in the art will recognize that the steps of the above exemplary embodiment may be performed in any suitable order.

In any of the aspects or embodiments described herein, the bacteria material used in the present method comprises material derived from a synthetic or wildtype mollicute bacteria. In any of the aspects or embodiments described herein, the bacteria material used the present method comprises material derived from synthetic or wildtype bacteria of the genus *Mycoplasma*. In any of the aspects or embodiments described herein, the bacteria material of the present method comprises material derived from synthetic or wild-type strains of *Mycoplasma pneumoniae*, *Mycoplasma gallisepticum*, *Mycoplasma pulmonis*, *Mycoplasma genitalium*, *Ureaplasma urealyticum*, *Mycoplasma hominis* or any combination thereof.

In any of the aspects or embodiments described herein, the method of manufacture further comprises combining the bacteria material or de-lipidated bacteria material with one or more suitable solvents, such as, e.g., saline solution.

In any of the aspects or embodiments described herein, the method of manufacture further comprises combining the bacteria material or de-lipidated bacteria material with one or more suitable buffers.

In any of the aspects or embodiments described herein, the method of manufacture further comprises combining the bacteria material or de-lipidated bacteria material with one or more suitable stabilizers, such as, e.g., sugar, gelatin, or sorbitol.

In any of the described aspects or embodiments, the method of manufacture further comprises combining the bacteria material or de-lipidated bacteria material with one or more suitable carriers.

In any of the described aspects or embodiments, the method of manufacture further comprises combining the bacteria material or de-lipidated bacteria material with one or more suitable preservatives, such as, e.g., anti-fungal agents.

In any of the described aspects or embodiments, the method of manufacture further comprises packing the bacteria material or de-lipidated bacteria material into a suitable delivery vehicle such as, e.g., aqueous solution, nonaqueous solution, tincture, pill, tablet, powder, nanoparticle, capsule, gel, cream, implant, or suppository.

In any of the described aspects or embodiments, the method of manufacture further comprises loading the bacteria material or de-lipidated bacteria material into a suitable patient-delivery apparatus, such as, e.g., a hypodermic syringe, intravenous drip, nasal syringe, pipette, eye dropper, inhaler, atomizer, or dermal patch.

In any of the described aspects or embodiments, the method of manufacture further comprises packaging the vaccine for shipment and storage.

In an additional aspect, the present description further provides methods of treating or preventing mollicute infections in a subject in need thereof, e.g., in a mammal such as a human (adult or adolescent). In any of the described aspects or embodiments, the method comprises administering to a subject in need thereof, e.g., a mammal or human, a therapeutically effective amount of vaccine, the vaccine comprising de-lipidated or non-lipidated bacteria material as described herein. In any aspect or embodiment described herein, at least a portion or all of the bacteria material is de-lipidated.

In any described aspect or embodiment, the vaccine may be administered parenterally, intravenously, intramuscularly, subcutaneously, nasally, dermally, orally, or rectally.

In any described aspect or embodiment, the vaccine may be administered using a hypodermic syringe, intravenous drip, nasal syringe, pipette, eye dropper, inhaler, atomizer, or dermal patch.

In a non-limiting exemplary embodiment, a vaccine comprising a solution of about 0.9% physiological saline, about 1000 µg/mL dLAMPs, and about 450 µg/mL MPLA is administered to a human patient parenterally by hypodermic needle injection, at a volume of about 0.5 mL.

EXAMPLES

Example 1: Identification of the Causal Factor of *Mycoplasma* VED

In order to identify the causal factor of *Mycoplasma pneumoniae* VED, a Triton™ X-114 phase partition was utilized to fractionate *M. pneumoniae* proteins into a detergent phase containing hydrophobic LAMP fraction, an aqueous fraction ("Aq") harboring mostly hydrophilic cytosolic proteins, and an insoluble fraction ("Ins") containing the insoluble Triton™ shell (Triton™-X-114-insoluble components) and a spontaneously forming, phospholipid-rich precipitate (described by Proft & Hermann). (Proft T & Hermann R. *Mol. Microbiol.* 1994 July; 13(2): 337-48.)

First, a pilot vaccination study using fractionated LAMPs was conducted in Specific Pathogen Free (SPF) BALB/c-strain mice, which resulted in VED after subsequent challenge with live virulent *M. pneumoniae* strain PI1428. This observation prompted the performance of a proteomic analysis (LC/MS-MS) of the LAMP fraction to enable identification of the causal factor of *Mycoplasma* VED. Gene products including lipoproteins, elongation factors, chaperone proteins, chaperonins, and cytoadherence proteins were identified using mass spectrometry in high abundance from the LAMP fraction. A breakdown of this component revealed lipoproteins were the most abundant. LC/MS-MS analysis revealed 22 lipoprotein gene products, representing all six lipoprotein families of *M. pneumoniae*. Specifically, Family 2 lipoproteins (paralogs of the immunodominant *Mycoplasma* gallisepticum nucleotide-binding virulence factor MslA) were found to be the most abundant in the lipoprotein fraction.

*Mycoplasma* lipoproteins have been previously shown to be potent immunostimulatory molecules, inducing the expression of inflammatory cytokines such as TNF-α, IL-6, and IL-1β following the recognition of their lipid moieties by TLR2/1 (triacylated lipoproteins) and/or TLR2/6 (diacylated lipoproteins) complexes. Likewise, vaccination with lipoproteins has previously been shown to induce a Th17 type immune response against *Streptococcus pneumoniae*, which is protective against this bacterium. Given that exuberant levels of IL-17A are associated with *M. pneumoniae* VED, it was hypothesized that *M. pneumoniae* lipoproteins, through immune stimulation via their lipid moieties, induce exuberant IL-17A production, which in turn accounts for *M. pneumoniae* VED.

Example 2. Testing the Hypothesis that *M. pneumoniae* Lipoprotein Lipid Moieties are the Cause of *M. pneumoniae* VED To test the hypothesis that *M. pneumoniae* lipoprotein lipid moieties are the cause of *M. pneumoniae* VED, Triton™ X-114-derived *M. pneumoniae* cell-extract fractions were treated with lipoprotein lipase (LPL) to hydrolyze the lipid moieties from the lipoproteins, thereby generating de-lipidated fractions (dLAMPs, dAq, and dIns).

*M. pneumoniae* strain PI1428 were cultured in FC medium (20% heat-inactivated horse serum, 5% yeast extract) in T-175 cell culture flasks at 37° C. Pelleted *M. pneumoniae* was washed with phosphate buffer solution (PBS) then solubilized in 5 mL TS-EDTA buffer solution (20 mM Tris, 150 mM NaCl, 5 mM ethylenediaminetetraacetic acid (EDTA) pH 7.6) containing 1 mM phenylmethylsulfonyl fluoride (PMSF) protease inhibitor, and 2% Triton™ X-114. The solution was centrifuged to pellet the insoluble phase. The soluble phase was transferred to a new tube, incubated, then centrifuged to separate the Triton™ X-114 detergent phase and aqueous phase.

The *M. pneumoniae* Triton™ X-114-derived LAMP, Aq, and Ins fractions were treated with 2500 units of *Burkholderia* sp. lipoprotein lipase (E.C. 3.1.1.34; Sigma Aldrich®) per 2 μg protein for 48 hours at 37° C. with shaking at 250 RPM on an orbital shaker.

Successful de-lipidation was assessed via a Toll-like receptor 2 (TLR-2) bioassay. Stimulation of murine macrophages with the LAMP fraction resulted in the production of large levels of TNF-α that were statistically higher than the levels produced by stimulation with Aq and Ins fractions. However, de-lipidation significantly reduced this fraction's ability to stimulate TNF-α production. (Surprisingly, the ability of the Aq fraction to stimulate TNF-α production was also significantly reduced by de-lipidation, suggesting that some lipoproteins may have sequestered to the Aq phase during Triton™ X-114 phase partitioning. De-lipidation did not affect the ability of the Ins fraction to stimulate TNF-α production.)

These fractions (LAMPs, dLAMPs; Aq, dAq; Ins, and dIns) were then utilized to intraperitoneally vaccinate mice using 50 μg of protein from the appropriate fraction per mouse, according to the following timeline: primary vaccination injection, followed 21 days later by a booster injection, followed 21 days later by a challenge injection of live virulent *M. pneumoniae*.

It was noticed that mice vaccinated with untreated, i.e., non-lipase-treated fractions began to display clinical signs consistent with sepsis, including piloerection, nose bulge, hunching, orbital tightening, and lethargy. These pathological signs were not observed in animals that were vaccinated with lipase-treated fractions (dLAMP, dAq, and dIns) or those that were sham vaccinated with a negative control. These data were used to generate a group clinical score. Fortunately, these signs diminished over time and were not noticeable by 48 hours post-vaccination. Regardless, these observations outline potential safety concerns in vaccine candidates that contain intact lipoproteins still bound to their lipid moieties. Given that these observations mirror the data from the TLR-2 bioassay, it is reasonable to conclude that the signs resulted from the over-stimulation of peritoneal immune cells by the lipid moieties of *M. pneumoniae* lipoproteins.

Vaccinated animals were challenged with live virulent *M. pneumoniae* three weeks after the booster shot. Four days after the challenge injection, the animals were humanely sacrificed, and lungs were collected for histopathology and *mycoplasma* recovery. It was observed that mice vaccinated with untreated LAMPs—but no other fraction—exhibited histopathological lung lesions that were statistically more severe than sham-vaccinated/challenged animals. Furthermore, vaccination with LAMPS did not reduce bacterial loads, nor did it reduce the number of *M. pneumoniae*-positive animals.

Vaccination with the de-lipidated dLAMPs, on the other hand, did not exacerbate lung pathology, demonstrating that the factor responsible for VED is the lipid moiety of *M. pneumoniae* lipoproteins. Additionally, *M. pneumoniae* was only recovered from 77 percent of mice vaccinated with dLAMPs, as opposed to from 95 percent of sham-vaccinated and 100 percent of LAMPs-vaccinated animals. Bacterial loads were significantly lower in dLAMP-vaccinated mice then in sham-vaccinated and LAMP-vaccinated mice, suggesting that dLAMPs include protective antigens that improve bacterial clearance.

Furthermore, vaccination of mice with 50 μg dLAMPs+ 20 μg of MPLA-SM adjuvant (per mouse), resulted in statistically reduced lung lesion scores when compared to sham-vaccinated mice.

Example 3. Establishing the Link Between IL-17A Stimulation and *M. pneumoniae* VED Measured serum levels of IL-17A were significantly higher in mice that were vaccinated with LAMPs and challenged, than sham-vaccinated and challenged mice. This observation is consistent with previous findings in studies reporting *M. pneumoniae* VED in SPF BALB/c mice. IL-17A-producing Th17 cells are known to increase in abundance in humans infected with *M. pneumoniae*. IL-17A-associated responses constitute a "double-edged sword" for the host, because they can protect against certain mucosal pathogens, but can also be exploited by other microorganisms to colonize the host. Indeed, IL-17A can be either protective or deleterious during *Streptococcus pneumoniae* infection. IL-17A has also been found to exacerbate disease in naïve BALB/c mice infected with *Mycoplasma pulmonis*. Mice vaccinated with dLAMPs and challenged did not display signs of VED, and have scrum levels of IL-17A that are significantly lower than in LAMP-vaccinated mice, but are similar to IL-17A levels in sham-vaccinated and infected mice. These data indicate a link between immune stimulation by lipoprotein lipid moieties, IL-17A levels, and exacerbated lung lesions in animals with VED.

In order to show a direct link between IL-17A and VED, a murine monoclonal anti-IL-17A antibody (Bio X Cell® clone 17F3) was utilized to neutralize IL-17A in the LAMP-vaccinated mouse model. An IgG isotype control (Bio X Cell® clone MOPC-21) was used as a control. The anti-IL-17A antibody treatment was given daily at a concentration of 150 µg/250 µL, starting the day before infection and continuing throughout the course of infection. As a negative control, another group of mice was given an isotype control antibody following the same concentration and schedule.

Lung lesion scores from LAMP-vaccinated, IL-17A-neutralized and infected mice were significantly lower than the lung lesions from LAMPs vaccinated and infected mice that received the isotype control, showing that IL-17A neutralization reduced VED-associated lung lesion severity. Surprisingly, bacterial loads from LAMP-vaccinated mice receiving the IL-17A-neutralizing antibody were significantly higher than LAMP-vaccinated mice receiving the isotype control, indicating IL-17A plays a complex role in the dynamics of *M. pneumoniae* disease.

IL-17A plays a major role in the induction of inflammation, as it serves to recruit neutrophils to the site of infection. While neutrophils are typically responsible for clearing bacterial infections, they have also been found to be dispensable for the clearance of *M. pneumoniae*. In fact, neutrophil recruitment by IL-17A has been shown to mediate disease exacerbation during *Mycoplasma pulmonis* infection. Although the finding that IL-17A exacerbates *M. pulmonis* disease was shown only in primary infection of naïve mice, and not as recall response as we show here, it was speculated that the mechanism for *M. pneumoniae* VED is similar to primary disease exacerbation by IL-17A during *M. pulmonis* infection. It was further speculated that stimulation of TLR-2 pattern recognition receptors by the lipid moieties of *M. pneumoniae* lipoproteins induces Th17 immune responses that result in overexuberant production of IL-17A upon re-stimulation during infection. Indeed, vaccination with lipoproteins has been shown to induce Th17 responses. In the case of *M. pneumoniae* infection, these Th17 responses are not protective, and the high IL-17A levels associated with these responses exacerbate disease by contributing to VED-causing immunopathology.

Example 4. Adjuvant-dLAMP-Vaccine Mediated Reduction in Lung Lesion

Figure 11:
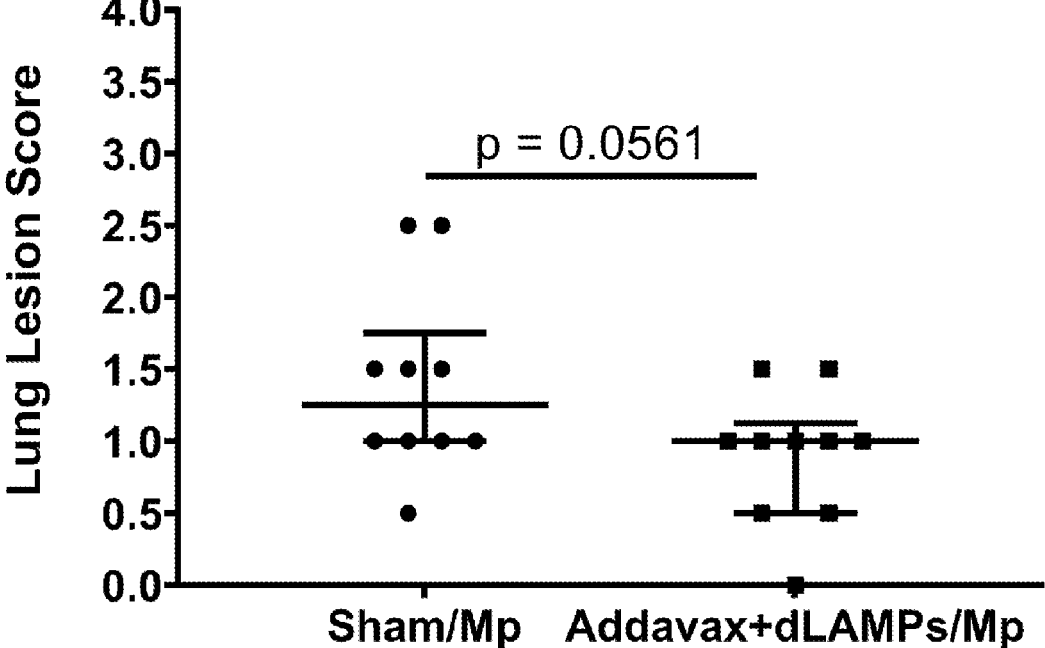
FIG. 11 is a graphical representation of experimental data, indicating that there is a significant reduction (p=0.0561) in bacterial-induced lesions in the lung when mice are vaccinated with dLAMP+adjuvant ("Addavax", which is a squalene based adjuvant) as compared to sham vaccination. Error bars indicate mean and SEM.

FIG. 11 illustrates that in mice treated with dLAMP vaccine, including a squalene-based adjuvant ("Addavax"), which is similar to MF59, there is a significant reduction (p=0.0561) in bacterial-induced lesions in the lung as compared to sham vaccination.

Figure 12:
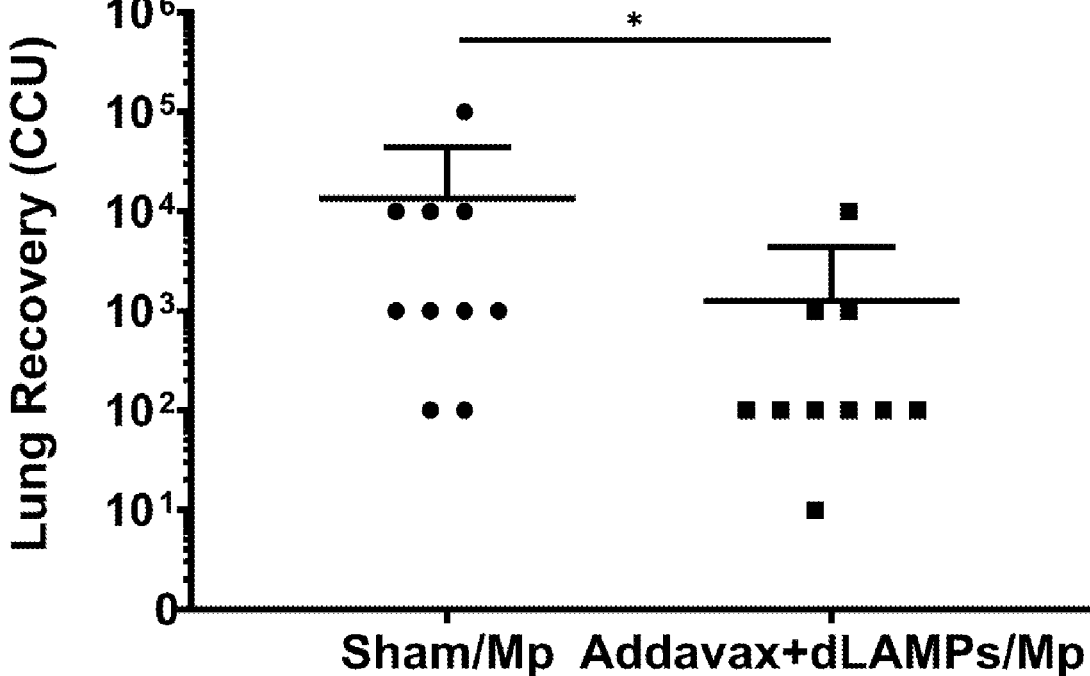
FIG. 12 is a graphical representation of experimental data, indicating that bacterial recovery in the lung (CCU) was significantly reduced (*) when mice are vaccinated with dLAMP+adjuvant ("Addavax", which is a squalene based adjuvant) as compared to sham vaccination. Error bars indicate mean and SEM.

Example 5. Adjuvant-dLAMP-Vaccine Mediated Decrease in Bacterial Recovery in the Lung FIG. 12 shows that in mice treated with dLAMP vaccine, including a squalene-based adjuvant ("Addavax"), which is similar to MF59, there is a significant reduction (*) in bacterial recovery in the lung (CCU) as compared to sham vaccination.

Figure 13:
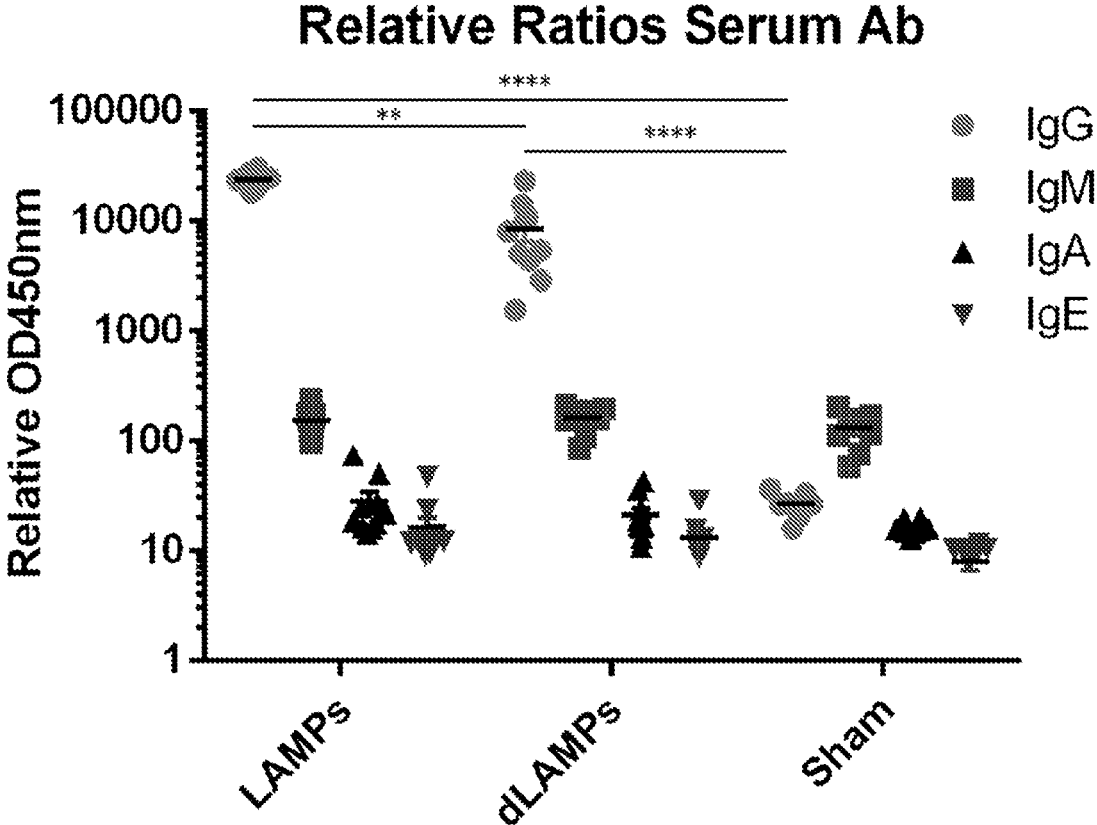
FIG. 13 is a graphical representation of experimental data, indicating *M. pneumoniae*-specific antibody titers in serum of mice challenged with LAMP protein, a dLAMP vaccine as described herein or sham vaccinated. The dLAMP vaccine produces robust anti-*M. pneumoniae* antibodies similar to LAMP proteins but without exacerbating disease state. Error bars indicate mean and SEM.

Example 6. Anti-*M. pneumoniae* Antibody Production in dLAMP-Vaccinated Mice FIG. 13 shows *M. pneumoniae*-specific antibody titers in serum of mice challenged with LAMP protein, a dLAMP vaccine as described herein or sham vaccinated. The dLAMP vaccine produces robust anti-*M. pneumoniae* antibodies similar to LAMP proteins but without exacerbating disease state. Error bars indicate mean and SEM.

The data indicate that only IgG was affected; being significantly higher in both LAMP and dLAMP-vaccinated mice versus sham vaccinated. The response to LAMP appears to be higher than dLAMP-vaccinated mice, which, without being bound by any particular theory, could be attributed to the added immunogenicity of the lipid moieties present. However, the data illustrate that both LAMPs and dLAMPs produce robust IgG responses and, as indicated above, dLAMPs do not exacerbate disease (unlike the LAMPs) and still drive robust antibody responses.

Those skilled in the art will recognize, or be able to ascertain using no more than routine experimentation, many equivalents to the specific embodiments of the invention described herein. Such equivalents are intended to be encompassed by the following claims. It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

What is claimed is:

1. A vaccine composition comprising a de-lipidated or non-lipidated mollicute bacteria material, wherein the de-lipidated or non-lipidated bacteria material includes at least one of:

a reduced amount of lipid moieties bound to membrane-associated lipoproteins relative to wildtype or untreated mollicute bacteria material;

a reduced amount of membrane-associated lipoproteins relative to wildtype or untreated mollicute bacteria material; or a combination thereof, wherein the mollicute bacteria material is derived from any bacteria of the genus *Mycoplasma* or the genus *Ureaplasma*.

2. The vaccine composition of claim 1, wherein the de-lipidated or non-lipidated bacteria material is derived from at least one of wildtype or synthetic strains of *Mycoplasma pneumoniae, Mycoplasma genitalium, Ureaplasma urealyticum, Mycoplasma hominis Mycoplasma* gallisepticum, *Mycoplasma pulmonis*, or any combination thereof.

3. The vaccine composition of claim 1, wherein the mollicute bacteria material is at least one of a non-ionic detergent-soluble whole-cell extract fraction or derived from any bacteria of the genus *Mycoplasma*.

4. The vaccine composition of claim 1, wherein the mollicute bacteria material is derived from bacteria of the species *Mycoplasma pneumoniae*.

5. The vaccine composition of claim 1, wherein the mollicute bacteria material is selected from at least one of: live whole-cell bacteria, inactivated whole-cell bacteria, whole-cell extract, lysate, detergent-soluble whole-cell extract fraction, water-soluble whole-cell extract fraction, detergent-insoluble whole-cell extract fraction, and any combination thereof.

6. The vaccine composition of claim 1, wherein at least one of:

the amount of membrane-associated lipoproteins is reduced at least about 50 percent relative to wildtype;

the lipid moieties bound to membrane-associated lipoproteins are reduced at least about 50 percent relative to wildtype; or a combination thereof.

7. The vaccine composition of claim 1, wherein at least one of:

the amount of membrane-associated lipoproteins is reduced at least about 70 percent relative to wildtype;

the lipid moieties bound to membrane-associated lipoproteins are reduced at least about 70 percent relative to wildtype; or a combination thereof.

8. The vaccine composition of claim 1, wherein at least one of:

the amount of membrane-associated lipoproteins is reduced at least about 85 percent relative to wildtype;

lipid moieties bound to membrane-associated lipoproteins are reduced at least about 85 percent relative to wildtype; or a combination thereof.

9. The vaccine composition of claim 1, having at least one of an undetectable amount of lipid moieties bound to membrane-associated lipoproteins;

an undetectable amount of membrane-associated lipoproteins; or a combination thereof.

10. The vaccine composition of claim 1, further comprising an adjuvant.

11. The vaccine composition of claim 10, wherein the adjuvant is monophosphoryl lipid A (MPLA).

12. The vaccine composition of claim 1, wherein: the vaccine composition further comprises at least one of a solvent, a buffer, a stabilizer, a carrier, a preservative, or a combination thereof; the vaccine composition is loaded into a hypodermic syringe, intravenous drip, nasal syringe, pipette, eye dropper, inhaler, atomizer, or dermal patch; or a combination thereof.

* * * * *